(12) United States Patent
Jessup

(10) Patent No.: US 11,471,167 B2
(45) Date of Patent: Oct. 18, 2022

(54) SELF-RELEASING TOURNIQUET

(71) Applicant: Mark Jessup, Stocksfield (GB)

(72) Inventor: Mark Jessup, Stocksfield (GB)

( * ) Notice: Subject to any disclaimer, the term of this patent is extended or adjusted under 35 U.S.C. 154(b) by 401 days.

(21) Appl. No.: 16/626,582

(22) PCT Filed: Jul. 3, 2018

(86) PCT No.: PCT/GB2018/051863
§ 371 (c)(1),
(2) Date: Dec. 26, 2019

(87) PCT Pub. No.: WO2019/008340
PCT Pub. Date: Jan. 10, 2019

(65) Prior Publication Data
US 2020/0121326 A1  Apr. 23, 2020

(30) Foreign Application Priority Data
Jul. 3, 2017 (GB) ...................................... 1710627

(51) Int. Cl.
*A61B 17/132* (2006.01)
*A61B 17/00* (2006.01)

(52) U.S. Cl.
CPC . *A61B 17/1322* (2013.01); *A61B 2017/00119* (2013.01); *A61B 2017/00398* (2013.01); *A61B 2017/00734* (2013.01)

(58) Field of Classification Search
CPC ........................... A61B 17/132; A61B 17/1322
See application file for complete search history.

(56) References Cited

U.S. PATENT DOCUMENTS

| | | | | |
|---|---|---|---|---|
| 6,149,666 A * | 11/2000 | Marsden | ............ | A61B 17/1322 606/203 |
| 6,213,939 B1 * | 4/2001 | McEwen | ............ | A61B 17/1355 600/202 |
| 6,589,268 B1 * | 7/2003 | McEwen | ............ | A61B 17/1355 606/202 |
| 8,043,327 B1 * | 10/2011 | Arias | ................. | A61B 17/1322 600/499 |
| 8,147,417 B2 * | 4/2012 | Gavriely | ............ | A61B 17/1325 600/499 |
| 8,926,651 B2 * | 1/2015 | McDonald | .............. | G01L 5/047 606/203 |
| 2008/0177159 A1 * | 7/2008 | Gavriely | ................ | A61B 90/92 600/301 |
| 2010/0234877 A1 * | 9/2010 | Pienkowski | ....... | A61B 17/1325 606/203 |

(Continued)

*Primary Examiner* — Ryan J. Severson

(57) ABSTRACT

A self-releasing tourniquet apparatus comprises an elongate strap and a housing. The strap has a first end and a second end and a plurality of holes arranged at substantially regular intervals along its length. The first end of the strap is connectable to the housing. The housing includes a projecting element sized to be received in one of the plurality of holes on the strap. The housing includes means for moving the projecting element from a first position to a second position after a predetermined period of time, and also includes timer means for measuring the predetermined period of time. In use, the strap is tensioned around a patient's limb when the projecting element is in the first position, and tension is released when the projecting element is in the second position.

11 Claims, 4 Drawing Sheets

(56) References Cited

U.S. PATENT DOCUMENTS

2012/0071917 A1* 3/2012 McDonald .............. G01L 5/102
                                                      116/212
2018/0271541 A1* 9/2018 Figueiredo ......... A61B 17/1327
2020/0121326 A1* 4/2020 Jessup ................ A61B 17/1322

* cited by examiner

SELF-RELEASING TOURNIQUET

PRIORITY

This is a US National Phase utility patent application relying upon and claiming priority to PCT/GB2018/051863, filed 2018 Jul. 3, and further claiming priority to GB 1710627.9, filed 2017 Jul. 3, which are incorporated herein for all purposes.

FIELD OF THE INVENTION

The invention relates to tourniquets for use in the drawing of blood from the limb of a patient, and more particularly to a self-releasing tourniquet which is able to automatically release the tension of the tourniquet.

BACKGROUND OF THE INVENTION

A tourniquet is a constricting device commonly used by medical professionals to control venous circulation for a period of time. When drawing blood from a patient's limb, or inserting a cannula into a vein, a tourniquet is often used to facilitate the siting of the needle in the vein. After drawing the required amount of blood, or after successful siting of the needle or cannula in the vein, the tourniquet is released to allow normal blood flow to return to the patient's limb.

According to WHO guidelines (WHO guidelines on drawing blood: best practices in phlebotomy, 2010) during a blood drawing procedure a tourniquet should not be left in place for longer than around two minutes. Prolonged application of a tourniquet can lead to haemoconcentration, a condition where blood pools at the venipuncture site and can lead to false blood results.

If a tourniquet is not released for an extended period of time, due to for example distraction of the medical personnel, then there is a risk of loss of function in the affected limb, as well as a risk of blood clots entering the patient's blood stream after the tourniquet is removed.

U.S. Pat. No. 8,043,327 describes an auto-release tourniquet apparatus which comprises a strap and a housing. One end of the strap is attached to the housing and the other end of the strap is attached to an anchor point which slots into the housing. The anchor point has a leaf spring attached which keeps the strap in place in the housing. When a timer expires, a mechanical strap releasing means pushes onto the leaf spring which allows the anchor point to be pushed away from the housing by a spring, thus releasing the tourniquet.

It would be desirable to provide an improved self-releasing tourniquet.

SUMMARY OF THE INVENTION

One aspect of the invention provides a self-releasing tourniquet apparatus comprising:
  an elongate strap having a first end and a second end and a plurality of holes arranged at substantially regular intervals along the length of the strap;
  a housing including a projecting element sized to be received in one of the plurality of holes on the strap;
  means for connecting the first end of the strap to the housing; and
  means for moving the projecting element from a first position to a second position after a predetermined period of time;
wherein the housing further includes timer means for measuring the predetermined period of time; and wherein, in use, the strap is tensioned around a patient's limb when the projecting element is in the first position, and tension is released when the projecting element is in the second position.

The projecting element may be a peg or a pin.

Preferably, the apparatus further comprises guide means for receiving the second end of the strap. Preferably the guide means is located adjacent the projecting element. The guide means may be in the form of a slot through which the second end of the strap passes, or a bar, underneath which the second end of the strap passes.

Preferably the projecting element is set at an angle to the housing of less than 90 degrees.

Preferably the means for moving the projecting element comprises means for rotating the projecting element in order to move the projecting element from the first position to the second position.

Preferably the means for rotating the projecting element comprises a motor and a worm drive and the projecting element is mounted on a worm gear. Alternatively, the means for rotating the projecting element includes a clockwork mechanism.

The first end of the strap may be permanently attached to the housing. Alternatively, the first end of the strap may be removably attachable to the housing.

Preferably the apparatus further includes at least one audible indicator which sounds after a predetermined period of time. The audible indicator may be a piezo electric sounder. A first audible indicator may sound after a first predetermined period of time and a second audible indicator may sound after a second predetermined period of time.

Preferably the apparatus further includes a visual indicator, for example a light or a flashing light which turns on after a predetermined period of time. The visual indicator may be an LED light.

The audible and/or visual indicators are preferably actuated before the projecting element is moved from the first position to the second position. The audible and/or visual indicators alert the medical professional that the tourniquet is still under tension, prompting manual removal of the apparatus from the patient's limb, by manually pulling the strap away from the projecting element. If the apparatus is not removed manually then the movement of the projecting element from the first position to the second position will automatically release the tension without any input from medical professionals.

Preferably, the housing includes a reset button. Manual actuation of the reset button preferably causes the projecting element to rotate from a release position to a tensioned position, and also resets the internal timer.

The apparatus may be single-use disposable. Alternatively, the strap may be single-use disposable and a new strap may be connectable to the housing for use with a new patient.

The apparatus may include a battery charge sensor and an audible alert may be activated when the level of battery charge falls below a threshold value.

The self-releasing tourniquet apparatus of the invention provides an improved, safer tourniquet for use in blood drawing procedures.

BRIEF DESCRIPTION OF THE DRAWINGS

In the drawings, which illustrate preferred embodiments of the invention by way of example.

DETAILED DESCRIPTION OF THE PREFERRED EMBODIMENTS

Figure 1:
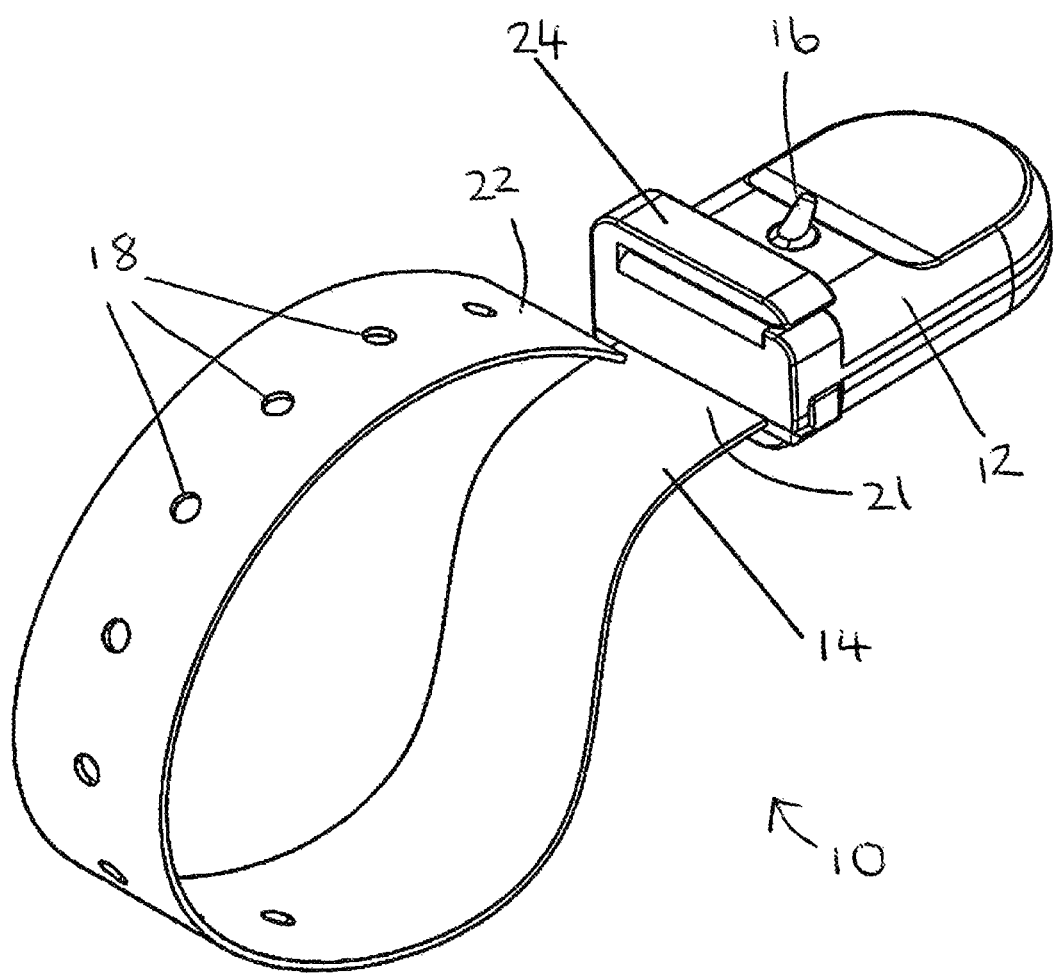
FIG. 1 illustrates a self-releasing tourniquet apparatus according to an embodiment of the invention.

As shown in FIG. 1, a self-releasing tourniquet apparatus 10 includes an elongate strap 14 and a housing 12. The strap 14 is connected to the housing 12 at one end. The strap 14 may be permanently connected to the housing 12 at one end 21, or may be releasably attached, meaning that a new strap 14 can be attached to the housing 12 for use with a new patient. The strap 14 includes a plurality of holes 18 regularly spaced along the length of the strap 14.

The housing 12 includes a projecting element or peg 16 located on the upper surface of the housing 12. The peg 16 is shaped to pass through the holes 18 in the strap 14. The housing 12 also includes an opening, or holding bar 24 through which the free end 22 of the strap 14 passes when securing the apparatus 10 to a patient's limb.

Figure 2:
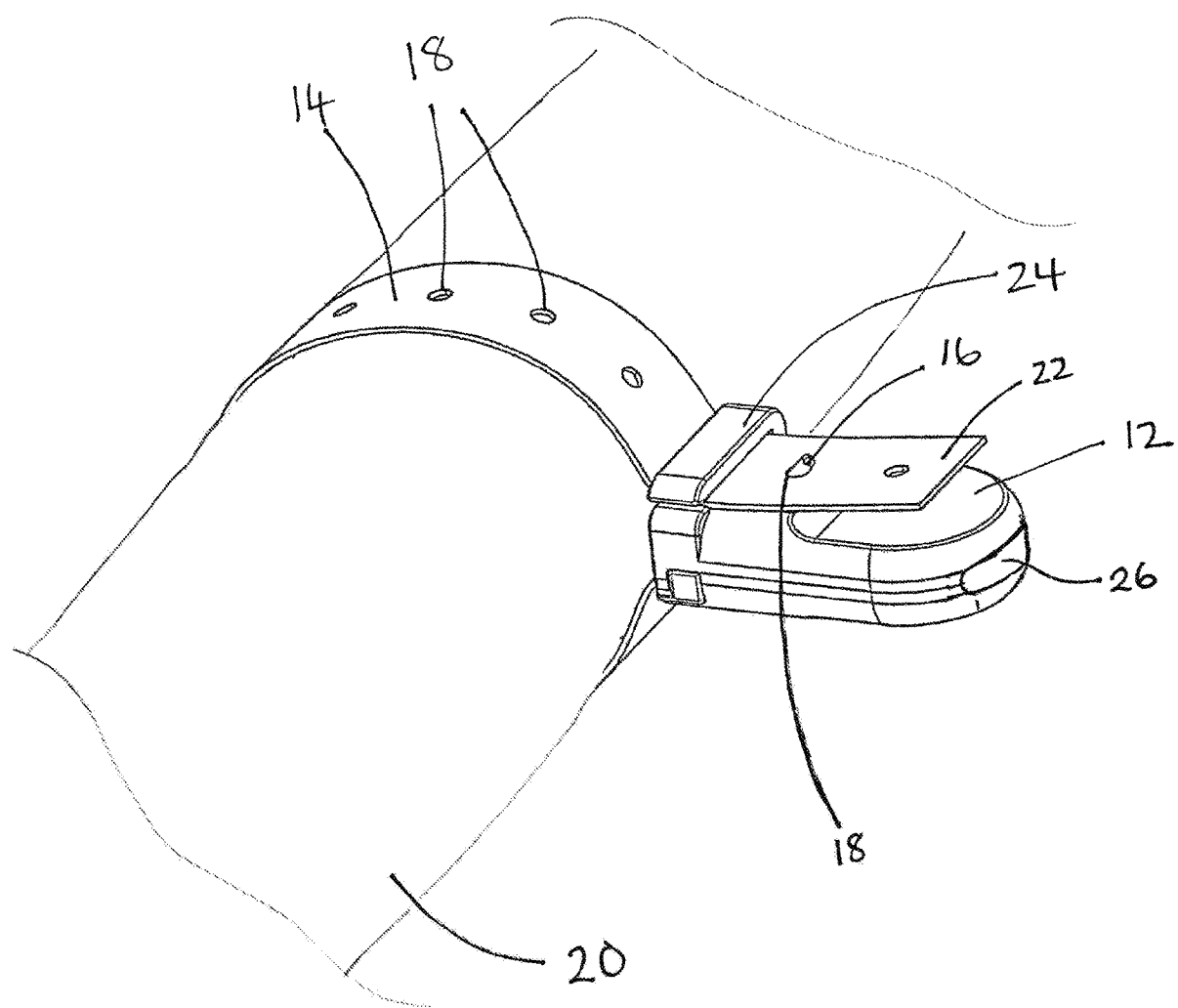
FIG. 2 illustrates the tourniquet apparatus of FIG. 1 in position around a patient's limb in a tensioned configuration.

FIG. 2 illustrates the tourniquet apparatus 10 secured around the limb 20 of a patient. As shown, the free end 22 of the strap 14 is passed underneath the holding bar 24, pulled taut, and then the most appropriate hole 18 is hooked over the peg 16 to secure the strap 14 in place.

As shown in FIG. 2, when the apparatus 10 is tensioned about the limb, the peg 16 is preferably in a position where it is angled away from the patient.

Figure 3:
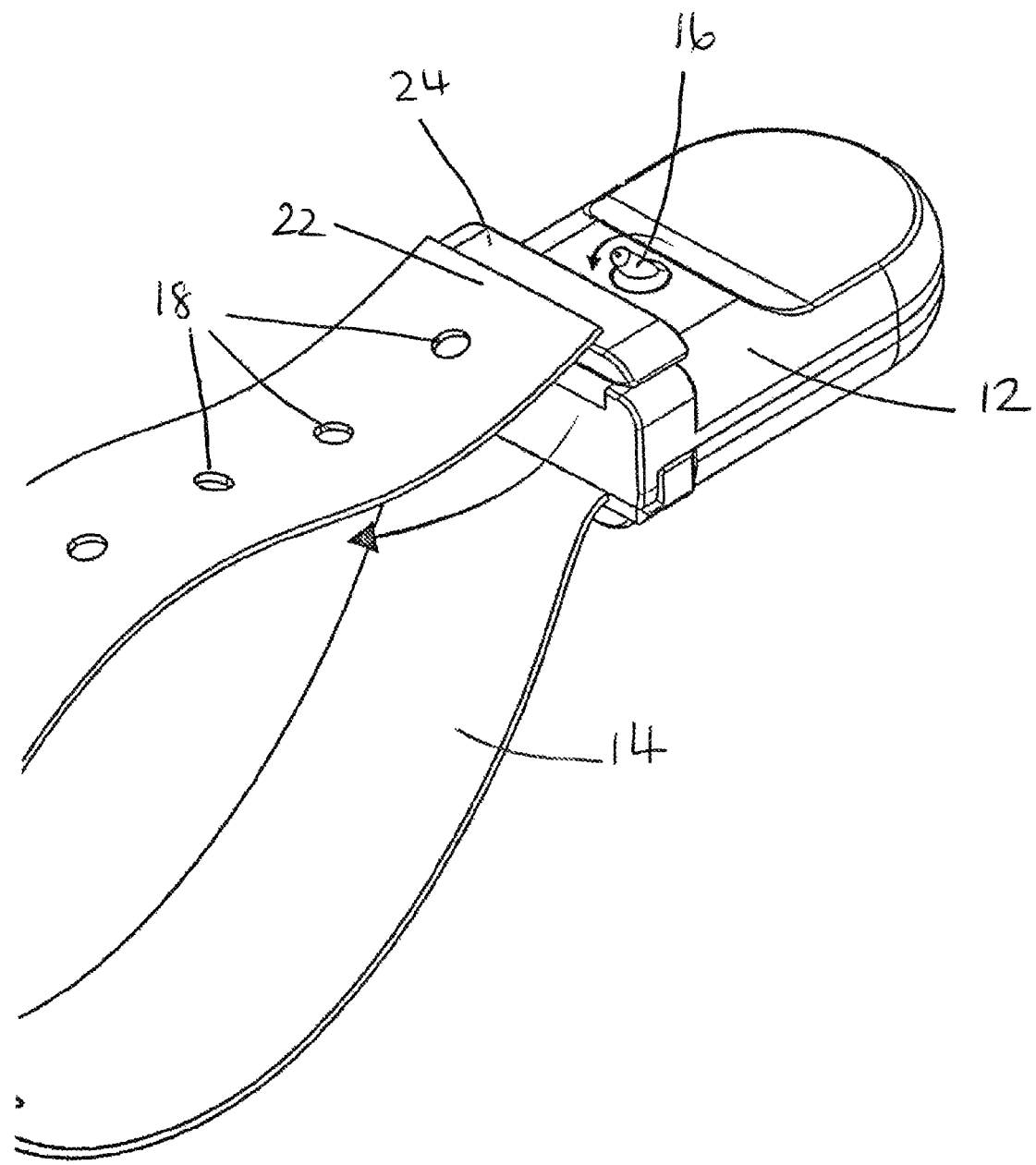
FIG. 3 illustrates the tourniquet apparatus of FIG. 1 with the projecting element in a release position.

FIG. 3 illustrates the second position, or release position, for the peg 16. In this example, the peg 16 is rotated from the first position illustrated in FIG. 2, where the strap is under tension, to a second position illustrated in FIG. 3, causing the tension in the strap 14 to be released.

Figure 4:
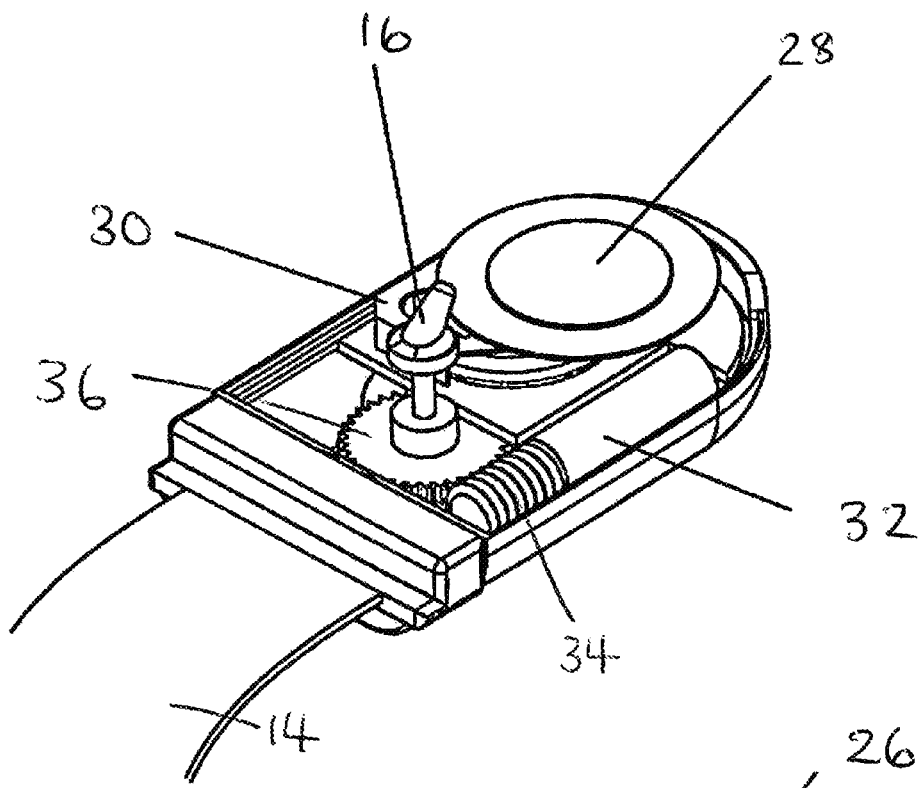
FIG. 4 illustrates the housing of the tourniquet of FIG. 1 with the outer casing removed, viewed from above.
Figure 5:
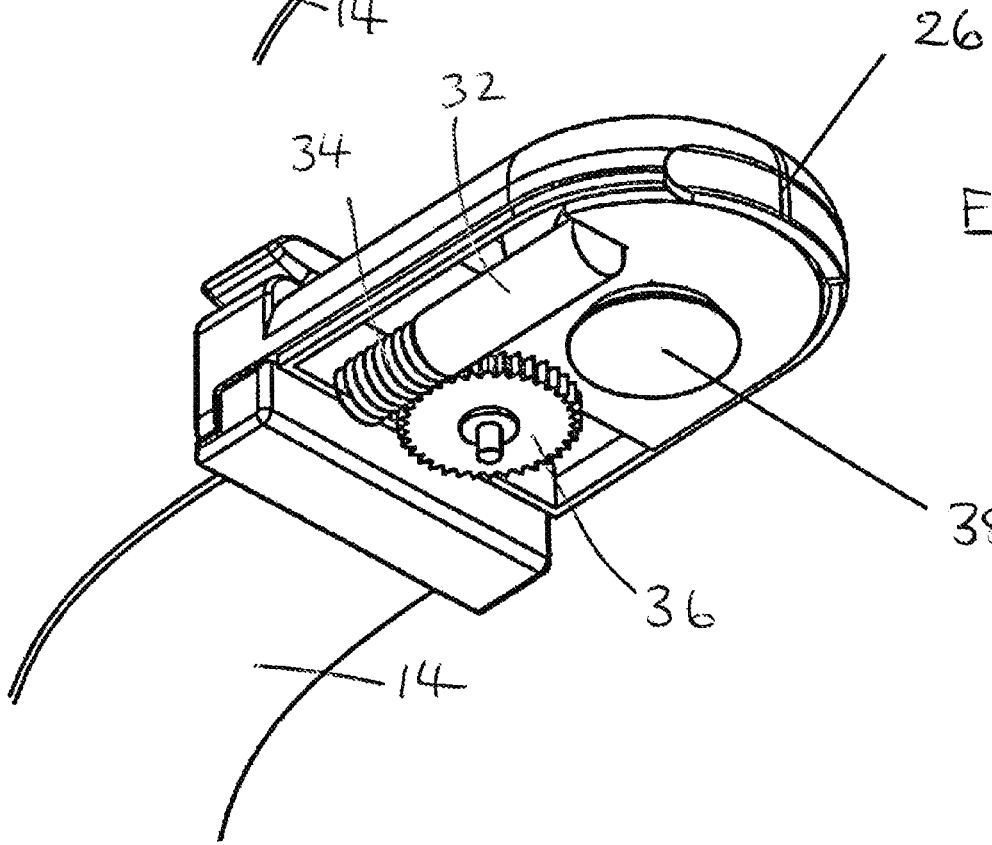
FIG. 5 illustrates the housing of the tourniquet of FIG. 1 with the outer casing removed, viewed from below.

FIGS. 4 and 5 illustrate the internal workings of the housing 12. In this example, the peg 16 is rotated using a worm drive. The peg 16 is mounted on a rotatable worm gear 36 which is driven by a worm 34. The worm 34 is turned by a motor 32 and the motor 32 is powered by a battery 30. The housing also includes a timer (not shown) which starts timing after the user presses an activation button 38 located on the underside of the housing 12. The motor 32 is actuated after a predetermined amount of time has been measured by the timer. In this example, the predetermined period of time may be a period of three minutes after pressing of the activation button 38 at the beginning of the procedure. The peg 16 cannot be manually manipulated back to the first position without resetting the apparatus using the activation button 38, meaning that the apparatus is automatically released.

The default setting is preferably where the peg 16 is positioned in the release position, angled towards the patient's limb (FIG. 2). Pressing of the activation button 38 on the underside of the housing 12 causes the rotation of the peg 16 to the first, or tensioned position and also restarts the timer.

In this example, the housing 12 also includes a piezo electric sounder 28 and an LED light indicator 26. The piezo electric sounder 28 and LED light indicator 26 are actuated after a time period which is shorter than the predetermined amount of time designated for the rotation of the peg 16. The sounding of an audible and/or visual LED alarm are designed to alert the medical professional that the tourniquet apparatus 10 is still in place on the patient and to remind them to remove the apparatus 10. It would be desirable for the audible and/or visual alarms to be actuated at around 90 seconds after the initial tensioning of the apparatus 10 on the patient's limb, although this time period could be reduced to 60 seconds. Preferably the audible and/or visual LED alarm will indicate for a short amount of time, for example a few seconds, before switching off.

At the end of the procedure the medical professional presses the activation button 28 which causes the peg 16 to rotate to the release position, releasing the tension in the strap 14.

The peg 16 then remains in the release position until the activation button 28 is pressed again, restarting the procedure.

The following example sets out the procedure for using the apparatus as part of a venipuncture procedure such as a blood draw or insertion of a cannula:

1. Medical professional presses activation button 38 on the apparatus 10;
2. Peg 16 rotates to first, tensioned, position, and timer starts to count;
3. Medical professional applies apparatus 10 to patient's limb and hooks an appropriate hole 18 over the peg 16;
4. Medical professional performs venipuncture procedure;
5. After the timer has counted 90 seconds following step 1, audible and visual alarms are temporarily triggered;
6a. Medical professional presses activation button 38; peg 16 rotates to second, release position, and tension in strap 14 is released; or
6b. Medical professional does not press the activation button 38; at 3 minutes following step 1 the peg 16 rotates to release position, and tension in strap 14 is released.

In a further example, a first audible alarm may be activated after the timer has counted 60 seconds following step 1, the first audible alarm may, for example, be a series of single beeps. A second audible alarm may then be activated after the timer has counted 120 seconds following step 2. The second audible alarm may, for example, be a series of double beeps. As with the previous example, if the activation button 38 has not been pressed at 3 minutes following step 1, then the peg 16 rotates to release position, and tension in strap 14 is released.

The apparatus may include a battery charge sensor (not shown). In the event of a low battery a different audible alert may be activated, for example a continuous beep or a continuous tone. This audible alert indicates to the medical professional that the auto-release may not function due to the low battery charge.

The apparatus may be a disposable, single use device. Alternatively, the housing 12 may be reusable and may be connectable to a new strap 14 for use with each new patient.

The invention claimed is:

1. A self-releasing tourniquet apparatus comprising:
    an elongate strap having a first end and a second end and a plurality of holes arranged at substantially regular intervals along the length of the strap;
    a housing including a projecting element sized to be received in one of the plurality of holes on the strap;
    means for connecting the first end of the strap to the housing; and
    means for moving the projecting element from a first position to a second position after a predetermined period of time;

wherein the housing further includes timer means for measuring the predetermined period of time; and wherein, in use, the strap is tensioned around a patient's limb when the projecting element is in the first position, and tension is released when the projecting element is in the second position.

2. A self-releasing tourniquet apparatus according to claim 1, the housing further comprising guide means for receiving the second end of the strap.

3. A self-releasing tourniquet apparatus according to claim 2, wherein the guide means comprises a bar underneath which the second end of the strap may be passed.

4. A self-releasing tourniquet apparatus according to claim 1, wherein the means for moving the projecting element comprises means for rotating the projecting element between the first position and the second position.

5. A self-releasing tourniquet apparatus according to claim 4, wherein the means for rotating the projecting element comprises a motor and a worm drive and the projecting element is mounted on a worm gear.

6. A self-releasing tourniquet apparatus according to claim 1, wherein the first end of the strap is releasably attachable to the housing.

7. A self-releasing tourniquet apparatus according to claim 1, the housing further comprising an audible indicator and means for actuating the audible indicator after a predetermined period of time.

8. A self-releasing tourniquet apparatus according to claim 7, wherein the audible indicator is a piezoelectric sounder.

9. A self-releasing tourniquet apparatus according to claim 1, the housing further comprising a visual indicator and means for actuating the visible indicator after a predetermined period of time.

10. A self-releasing tourniquet apparatus according to claim 9, wherein the visual indicator is an LED.

11. A self-releasing tourniquet apparatus according to claim 1, the housing further including an activation switch, wherein the activation switch is adapted to restart the timer means and move the projecting element from the second position to the first position.

* * * * *